(12) United States Patent
Farhadi

(10) Patent No.: US 9,610,005 B2
(45) Date of Patent: Apr. 4, 2017

(54) METHODS, DEVICES AND SYSTEMS FOR IMPROVED HYGIENE DURING ENDOSCOPIC PROCEDURES

(71) Applicant: Ashkan Farhadi, Irvine, CA (US)

(72) Inventor: Ashkan Farhadi, Irvine, CA (US)

( * ) Notice: Subject to any disclaimer, the term of this patent is extended or adjusted under 35 U.S.C. 154(b) by 0 days.

(21) Appl. No.: 14/924,602

(22) Filed: Oct. 27, 2015

(65) Prior Publication Data

US 2016/0045099 A1 Feb. 18, 2016

Related U.S. Application Data

(63) Continuation-in-part of application No. 14/027,245, filed on Sep. 16, 2013, and a continuation-in-part of application No. 14/215,005, filed on Mar. 16, 2014.

(60) Provisional application No. 61/847,984, filed on Jul. 18, 2013, provisional application No. 61/885,500, filed on Oct. 2, 2013.

(51) Int. Cl.
*A61B 1/00* (2006.01)

(52) U.S. Cl.
CPC ...... *A61B 1/00144* (2013.01); *A61B 1/00137* (2013.01); *A61B 1/00142* (2013.01)

(58) Field of Classification Search
CPC ............ A61B 1/00135; A61B 1/00142; A61B 1/00144; A61B 1/00151
USPC ........................................ 600/121, 124, 125
See application file for complete search history.

(56) References Cited

U.S. PATENT DOCUMENTS

| 3,449,037 | A | | 6/1969 | Koester |
| 3,805,770 | A | | 4/1974 | Okada |
| 4,646,722 | A | | 3/1987 | Silverstein et al. |
| 4,809,678 | A | * | 3/1989 | Klein ................ A61B 1/00142 600/121 |
| 4,886,049 | A | | 12/1989 | Darras |

(Continued)

FOREIGN PATENT DOCUMENTS

| AU | 651843 B2 | 8/1994 |
| WO | WO-97-04828 A1 | 5/1998 |

(Continued)

OTHER PUBLICATIONS

Alvarado et al., "Microbiologic assessment of disposable sterile endoscopic sheaths to replace high-level disinfection in reprocessing: A prospective clinical trial with nasopharygoscopes." American journal of infection control 37.5 (2009): 408-413.

(Continued)

*Primary Examiner* — Matthew F Desanto
(74) *Attorney, Agent, or Firm* — Venable LLP; Michele V. Frank

(57) ABSTRACT

According to some embodiments of the invention, an endoscope sleeve comprises a sleeve defining a lumen for accepting an endoscope in a slidable manner, the sleeve having a proximal end configured to accept the endoscope and a distal end configured to be slidably disposed over the endoscope, wherein the sleeve comprises a compact configuration and an extended configuration. The endoscope sleeve further comprises a retainer configured to be detachably attached to the sleeve, wherein in the compact configuration the retainer is attached to the sleeve and in the extended configuration the retainer is detached from the sleeve allowing the sleeve to be extendable over the endoscope.

22 Claims, 17 Drawing Sheets

(56) References Cited

U.S. PATENT DOCUMENTS

| | | | |
|---|---|---|---|
| RE34,002 E * | 7/1992 | Adair | A61B 1/00142 348/373 |
| 5,159,919 A | 11/1992 | Chikama | |
| 5,198,894 A | 3/1993 | Hicks | |
| 5,217,001 A | 6/1993 | Nakao et al. | |
| 5,458,132 A | 10/1995 | Yabe et al. | |
| 5,496,259 A | 3/1996 | Perkins | |
| 5,554,098 A | 9/1996 | Yabe et al. | |
| 5,569,159 A | 10/1996 | Anderson et al. | |
| 5,569,161 A | 10/1996 | Ebling et al. | |
| 5,630,782 A | 5/1997 | Adair | |
| 5,702,344 A | 12/1997 | Silverstein | |
| 5,733,242 A | 3/1998 | Rayburn et al. | |
| 5,795,404 A | 8/1998 | Murphy et al. | |
| 5,863,286 A | 1/1999 | Yabe et al. | |
| 5,924,977 A | 7/1999 | Yabe et al. | |
| 5,941,815 A | 8/1999 | Chang | |
| 6,149,581 A | 11/2000 | Klingenstein | |
| 6,293,907 B1 | 9/2001 | Axon et al. | |
| 6,293,909 B1 | 9/2001 | Chu et al. | |
| 6,530,881 B1 | 3/2003 | Ailinger et al. | |
| 6,749,601 B2 * | 6/2004 | Chin | A61B 46/13 206/363 |
| 6,793,621 B2 | 9/2004 | Butler et al. | |
| 6,830,545 B2 | 12/2004 | Bendall | |
| 6,852,077 B2 * | 2/2005 | Ouchi | A61B 1/00142 600/122 |
| 6,852,078 B2 | 2/2005 | Ouchi | |
| 6,869,393 B2 | 3/2005 | Butler | |
| 6,908,428 B2 | 6/2005 | Aizenfeld et al. | |
| 7,625,207 B2 * | 12/2009 | Hershey | A61C 1/16 433/100 |
| 7,695,428 B2 | 4/2010 | Machida | |
| 7,905,830 B2 | 3/2011 | Stefanchik et al. | |
| 8,262,561 B2 | 9/2012 | Kress | |
| 8,465,419 B2 | 6/2013 | Moriyama | |
| 8,647,261 B2 * | 2/2014 | Jaworek | A61M 25/0111 600/114 |
| 2003/0172941 A1 | 9/2003 | Streifinger et al. | |
| 2003/0229269 A1 | 12/2003 | Humphrey | |
| 2004/0143161 A1 | 7/2004 | Baror et al. | |
| 2006/0111611 A1 | 5/2006 | Eizenfeld et al. | |
| 2007/0066869 A1 | 3/2007 | Hoffman | |
| 2007/0112250 A1 * | 5/2007 | Kura | A61B 1/00135 600/114 |
| 2007/0260117 A1 | 11/2007 | Zwolinski et al. | |
| 2009/0182198 A1 | 7/2009 | Skerven et al. | |
| 2010/0010308 A1 | 1/2010 | Braun et al. | |
| 2012/0010468 A1 | 1/2012 | Afridi | |
| 2012/0283663 A1 | 11/2012 | Delegge | |
| 2014/0150782 A1 | 6/2014 | Vazales et al. | |

FOREIGN PATENT DOCUMENTS

| | | |
|---|---|---|
| WO | WO-01-00080 A2 | 1/2001 |
| WO | WO-2004-008950 A1 | 1/2004 |
| WO | WO-2005-110185 A1 | 11/2005 |
| WO | WO-2014-092650 A1 | 6/2014 |

OTHER PUBLICATIONS

Baker et al., "Evaluation of endoscope sheaths as viral barriers." The Laryngoscope 109.4 (1999): 636-639.
Kovaleva et al., "Is bacteriologic surveillance in endoscope reprocessing stringent enough?." Endoscopy 41.10 (2009): 913.
Noronha et al., "A 21st century nosocomial issue with endoscopes." BMJ: British Medical Journal 348 (2013).
Pajkos et al., "Is biofilm accumulation on endoscope tubing a contributor to the failure of cleaning and decontamination?." Journal of Hospital Infection 58.3 (2004): 224-229.

* cited by examiner

METHODS, DEVICES AND SYSTEMS FOR IMPROVED HYGIENE DURING ENDOSCOPIC PROCEDURES

CROSS-REFERENCE TO RELATED APPLICATIONS

This application is a continuation-in-part of U.S. patent application Ser. No. 14/027,245 entitled "Method and Device for Improved Hygiene During Endoscopic Procedures" filed on Sep. 16, 2013, which claims the benefit of priority to U.S. Patent Application No. 61/847,984 entitled "Endoscope Cover" filed on Jul. 18, 2013. This application is also a continuation-in-part of U.S. patent application Ser. No. 14/215,005 entitled "Method and Device for Improved Hygiene During using Endoscopic accessory tools" filed on Mar. 16, 2014, which claims the benefit of priority to U.S. Patent Application No. 61/885,500 entitled "Method and Device for Improved Hygiene During using Endoscopic accessory tools" filed on Oct. 2, 2013. The contents of the above-listed patent applications are hereby incorporated by reference in their entireties.

FIELD OF INVENTION

This invention relates generally to methods and devices that improve hygiene in the endoscopic examination of body organs, the gastrointestinal tract in particular. This invention incorporates a sleeve for an endoscope that remains outside of the patient's body during an endoscopic exam, and is configured to keep the endoscope clean prior to insertion into the patient's body. It is also designed to retain any bodily matter within the sleeve itself upon removal of the endoscope from the patient's body.

BACKGROUND

An endoscope is a well-known optical system for evaluation of internal organs. Most endoscopic procedures are not sterile procedures. After completion of a cleansing process, the endoscope is handled as a clean object. It is usually kept in clean spaces, transported to the procedure room by a clean hand with or without gloves, placed on a clean surface for assembly to the light source, placed on a bed sheet in the case of a colonoscopy, and then lubricated and inserted into a body cavity. During the procedure, the shaft of the endoscope is usually held by the endoscopist for insertion, withdrawal, and manipulation. The endoscope could be inserted and withdrawn multiple times during a single endoscopic procedure, meaning that with each withdrawal, the shaft of the endoscope touches the external environment including the bedding, examination table and the patient's external body surfaces. The endoscope is occasionally held by an assistant during the examination base of the procedure. After withdrawal from a body cavity, the endoscope is handled as a contaminated object and is taken to the cleaning room where it is to be cleaned for the next procedure. To improve and upkeep the sanitization aspect of endoscopic procedures, endoscopic centers follow a set of policies set in place by the endoscopic center's internal policies or regulatory agencies.

SUMMARY

According to some embodiments of the invention, an endoscope sleeve comprises a sleeve defining a lumen for accepting an endoscope in a slidable manner, the sleeve having a proximal end configured to accept the endoscope and a distal end configured to be slidably disposed over the endoscope, wherein the sleeve comprises a compact configuration and an extended configuration. The endoscope sleeve further comprises a retainer configured to be detachably attached to the sleeve, wherein in the compact configuration the retainer is attached to the sleeve and in the extended configuration the retainer is detached from the sleeve allowing the sleeve to be extendable over the endoscope.

According to some embodiments, the sleeve comprises a first sleeve and the retainer comprises a second sleeve, and the second sleeve defines the lumen for accepting the endoscope. The second sleeve has a length that is less than a length of the first sleeve.

According to some embodiments, the first sleeve and the second sleeve define a cavity therebetween. A fluid port can be in fluid connection with the cavity. The fluid port can be connected to at least one of the first sleeve and the second sleeve.

According to some embodiments, the distal end of the sleeve comprises a closure for closing the lumen. The closure can be a re-sealable zipper.

According to some embodiments, the proximal end of the sleeve includes a collar configured to secure the sleeve to the endoscope. The proximal end of the sleeve can further comprise a sealing mechanism to seal the collar to the endoscope with a reversible, liquid-tight seal. The sealing mechanism can comprise at least one of an elastomeric material, self-fusing silicon tape, hook and loop fastener, purse string closure, tie-on closure, or pressure sensitive adhesive tape.

According to some embodiments, the endoscope sleeve further comprises a wiping material disposed on an inner surface of the sleeve. According to some embodiments, the endoscope sleeve further comprises a wiping material disposed within the cavity. The wiping material can comprise at least one of a hydrophilic foam, gauze, an unwoven material, or flox.

According to some embodiments, the sleeve comprises a first sleeve and the retainer comprises a second sleeve including a perforation, wherein the first sleeve is detachable at the perforation.

According to some embodiments, the retainer comprises a strap, wherein the strap has a length that is less than a length of the sleeve.

According to some embodiments, at least a portion of the sleeve comprises at least one of a transparent material and an elastomeric material.

According to some embodiments, at least a portion of the sleeve comprises a flexible material.

According to some embodiments, the sleeve in the extended configuration has a length longer than the length of the sleeve in the compact configuration.

According to some embodiments, the sleeve has the compact configuration when the retainer is attached to the sleeve.

According to some embodiments, the second sleeve includes a proximal end and a distal end, and the proximal ends of the first and second sleeves are attached and the distal end of the second sleeve is removably attached to the first sleeve away from the proximal end of the first sleeve. According to some embodiments, the second sleeve is removably attached at or between a midsection and the distal end of the first sleeve. According to some embodiments, the sleeve comprises a line of weakness extending from the proximal end to the distal end, wherein the line of weakness allows the sleeve to be separated along the line of weakness.

According to some embodiments, at least a portion of the sleeve comprises a material that has reduced friction when sliding over the endoscope.

According to some embodiments, the endoscope sleeve further comprised an annular squeegee disposed within the lumen, wherein the annular squeegee has an inner circumference and an outer circumference, wherein the annular squeegee is attached to an inner surface of the sleeve along the outer circumference of the annular squeegee.

According to some embodiments of the invention, a method for enhancing hygiene during transport and/or use of an endoscope, the endoscope having a shaft and a distal end, the shaft comprising a proximal shaft portion and a distal shaft portion, comprises providing a sleeve defining a lumen for accepting the endoscope, the sleeve having a proximal portion and a distal portion, the sleeve further having a retainer, a portion of the retainer being removably attached to the sleeve to maintain at least a portion of the sleeve in a compact format. The method further comprises positioning the sleeve on the endoscope, extending the distal portion of the sleeve beyond the distal shaft portion and the distal end of the endoscope, and sealing the distal portion of the sleeve, thereby enclosing the shaft and distal end of the endoscope within the lumen. The extending the distal portion of the sleeve detaches the portion of the retainer from the sleeve so that at least a portion of the sleeve expands from a compact form to an unpacked form.

According to some embodiments, the step of positioning further comprises securing a proximal portion of the sleeve to the endoscope, wherein the endoscope further comprises a conical connection to the proximal shaft portion, and wherein securing the proximal portion of the sleeve to the endoscope comprises securing the proximal portion of the sleeve to the endoscope at the conical connection or at the proximal shaft portion.

According to some embodiments, the sleeve further defines a cavity for maintaining a fluid separate from the lumen when the portion of the sleeve is in the compact form, and extending the distal portion of the sleeve releases the fluid in the cavity into the lumen when the portion of the sleeve is in the unpacked form.

According to some embodiments, the sleeve further defines a cavity, and extending the distal portion of the sleeve opens the cavity to the lumen.

According to some embodiments, the method further comprises transporting the endoscope and the sleeve to a location for use of the endoscope, opening the distal portion of the sleeve, and pulling the distal portion of the sleeve toward the proximal shaft portion of the endoscope to expose the distal shaft portion and the distal end of the endoscope for use.

According to some embodiments, the method further comprises introducing a lubricating material into the lumen at least one of before or after extending the distal portion of the sleeve.

According to some embodiments, the method further comprises disposing a wiping material in the lumen, and gripping a portion of the sleeve surrounding the wiping material and sliding the portion of the sleeve surrounding the wiping material over the shaft of the endoscope to lubricate or wipe the shaft of the endoscope.

According to some embodiments, the method further comprises disposing a wiping material in the lumen, gripping a portion of the sleeve surrounding the wiping material, and moving the distal end and shaft of the endoscope into or out of a body cavity.

According to some embodiments, the method further comprises extending the distal portion of the sleeve beyond the distal shaft portion and distal end of the endoscope after the endoscope is withdrawn from the body cavity, and sealing the distal portion of the sleeve, thereby enclosing the shaft and distal end of the endoscope within the lumen.

According to some embodiments, the sleeve has a midportion between the proximal portion and the distal portion, and extending the distal portion of the sleeve expands the midportion of the sleeve from the compact form to the unpacked form.

According to some embodiments, the step of positioning further comprises securing a proximal portion of the sleeve to the endoscope.

BRIEF DESCRIPTION OF THE DRAWINGS

Further objectives and advantages will become apparent from a consideration of the description, drawings, and examples.

DETAILED DESCRIPTION

Figure 1:
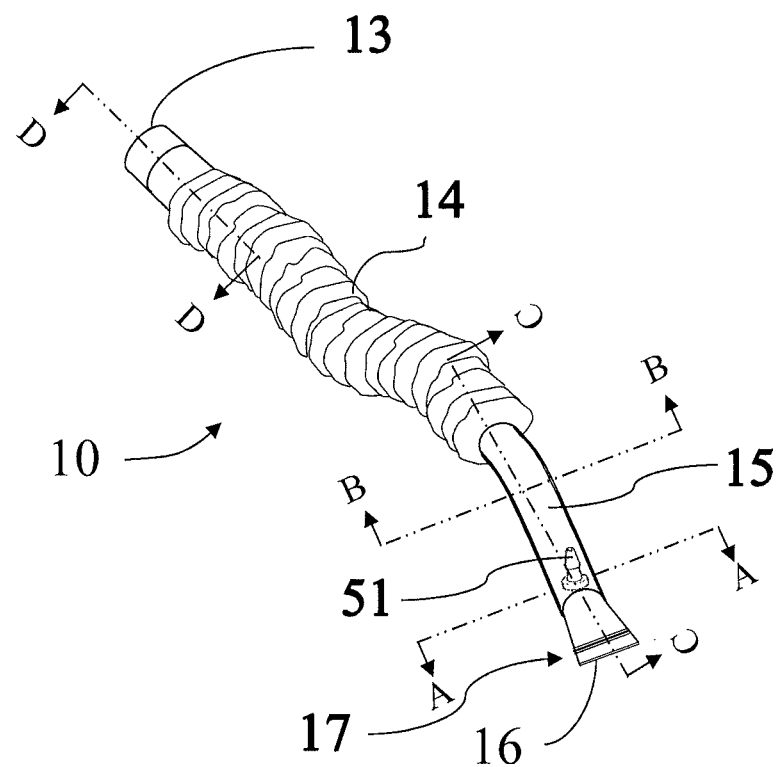
FIG. 1 is a schematic illustration showing the endoscope sleeve in the compact format prior to being mounted over the shaft of an endoscope.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention.

The endoscope sleeve of the present invention covers a variety of medical instruments and provides improved endoscopic sanitization. Those skilled in the art will recognize that the term endoscope refers to an instrument for visualizing or accessing the interior of a body cavity. Specifically, the covering according to some embodiments of the present invention is suitable for use on colonoscopes, upper G.I. fiberscopes, enteroscopes, sigmoidoscopes, bronchofiberscopes, and the like.

The endoscope sleeve embodying this invention enhances sanitization during endoscopic procedure and facilitates the endoscopic procedure in general. According to some embodiments of the invention, the endoscope sleeve comprises two elongated, coaxial, flexible, open-ended, disposable tubular sleeves of different lengths. The inner tube can be relatively shorter and is called the inner sleeve and is disposed within the outer tube that can be relatively longer and is called the outer sleeve. The inner sleeve and outer sleeve can both terminate proximally in the sleeve proximal cuff The distal end of the inner sleeve can connect to the distal end of the outer sleeve. The comparatively shorter length of the inner sleeve to the outer sleeve can result in pleating of the outer sleeve. This is when the endoscope sleeve is in a compact state. Unpacking can occur when the distal end of the outer sleeve and inner sleeve are disconnected, and the outer sleeve can be unfolded to its original size. The outer sleeve can be sized to removably receive an endoscope shaft and can be designed with a length sufficient to extend beyond the full length of an endoscope shaft. A function of the inner sleeve can be to keep the outer sleeve in a compact format.

The endoscope sleeve in its compact format can be pulled over the distal end of an endoscope shaft through the proximal opening of the sleeve. The endoscope sleeve can be pulled proximally along the endoscope shaft until it reaches the proximal portion of the endoscope shaft or the graduated endoscope junction that serves to connect the endoscope knob portion to the endoscope shaft. According to some embodiments of the invention, the proximal end portion of the endoscope sleeve terminates in a proximal sleeve cuff that provides a cuff seal which is securely attached to the proximal endoscope shaft or the graduated endoscope junction and creates a liquid-tight seal with the endoscope shaft at the site of attachment.

The proximal sleeve cuff seal can include an elastomeric collar or fluted proximal end portion provided with a closure mechanism that includes at least one of the following: a hook-and-loop fastener, a pressure sensitive adhesive provided on the inner surface, a purse string closure, a tie on closure, a pressure sensitive tape on the outer surface, and self-fusing silicon tape or a combination thereof After securing the proximal sleeve cuff, the endoscope sleeve can be changed into its unpacked format. To achieve this format, the distal portion of the outer sleeve is pulled toward the distal portion of the endoscope shaft. By doing this the distal end portion of the inner sleeve can be disconnected from the distal end portion of the outer sleeve along a perforated line 23. After being released from the inner sleeve, the outer sleeve can be unfolded and pulled over the endoscope shaft until it covers the endoscope shaft in its entirety. The outer sleeve can then be reversibly moved back and forth along the endoscope shaft.

The interior surface of the outer sleeve can be made from a material that creates minimal friction over the endoscope shaft. The exterior surface of the outer sleeve can be made from a material that creates adequate friction with the endoscopist's glove, particularly at its distal end portion. This indicates that the distal end portion of the endoscope sleeve can be grasped by the endoscopist and can be retracted back and forth over the endoscope shaft.

The interior surface of the outer sleeve at the distal end portion can be supplemented with an elongated, flexible, open-ended wiping material adhered to the interior surface of the outer sleeve at the distal end portion. This allows the endoscope shaft to be grasped by the tubular wiping material within the distal end portion of the outer sleeve. The distal end portion of the outer sleeve can be moved together with the wiping material in a loose slidable fashion over the endoscope shaft and can wipe the surface of the endoscope shaft when the distal end portion of the outer sleeve is being grasped loosely or can be used to grasp the endoscope shaft to move the endoscope shaft into or out of the body cavity when the distal end portion of the outer sleeve is being grasped firmly. The tubular wiping material may be composed of a hydrophilic foam, gauze, unwoven material, flox, other similar materials, or a combination thereof.

According to some embodiments of the invention, the distal end portion of the outer sleeve is provided with a lubricant port that is used to fill the space between the outer sleeve and the inner sleeve with lubricant material while the endoscope cover is in its compact format. The lubricant port can be used to inject lubricant material inside the outer sleeve over the endoscope shaft in its unpacked format.

The distal end of the outer sleeve is also provided with a closure mechanism that enables the sealed closure of the distal end of outer sleeve. This closure mechanism can be a re-sealable zipper, tie down, pull string, or other similar mechanism, or a combination thereof.

The distal end portion of the outer sleeve can be supplied with one or multiple annular squeegees on the interior surface. An annular squeegee is a donut-shaped, rubbery protrusion, positioned at an angle to the axis of the distal end portion of the outer sleeve, attached irremovably to the interior surface at the distal end portion of the outer sleeve proximal or distal to the tubular wiping material. The inner ring diameter of the annular squeegee can be sized such that the inner ring creates loose circumferential contact over the endoscope shaft. The angle, shape, and material properties of the annular squeegee can provide a low friction interface between the endoscope shaft and the annular squeegee, and can provide a means for cleaning the endoscope shaft when the distal end portion of the outer sleeve is moved in a loose slidable manner over the endoscope shaft toward the distal end portion of the endoscope shaft during endoscope withdrawal.

The endoscope sleeve can be provided with a line of weakness along the entire length of the tube that can be used to tear open the outer and/or inner sleeve for removal of the endoscope shaft out of the endoscope sleeve in a sideways, partial or complete manner.

The outer sleeve, particularly the mid portion of the outer sleeve, can be made from transparent material such as a polyolefin film.

The distal end portion of the outer sleeve can be made from a less flexible, opaque material. The distal end portion may be molded or cast from an elatomeric material such as silcone, urethane rubber or non-elatomeric material supplied with one or all three components of tubular wiping material, annular squeegee, and lubricant dispenser.

The outer sleeve can have a length sufficient to extend beyond the full length of an endoscope shaft. The distal opening of the outer sleeve stays distal to the distal tip of the endoscope shaft in its unpacked format of endoscope cover during storage and transportation.

In addition, a method is disclosed for improved hygiene in the endoscopic examination of a patient's body cavity comprising the following steps. After the cleaning of an endoscope in an endoscope cleaning room, the distal end of the endoscope shaft is inserted into the proximal opening of the endoscope sleeve in its compact format. The endoscope sleeve can be pulled proximally along the endoscope shaft until it reaches either the proximal portion of the endoscope shaft or the graduated endoscope junction that connects the endoscope knob portion to the endoscope shaft. The proximal sleeve cuff is then securely attached to the proximal endoscope shaft or the graduated endoscope junction to create a liquid-tight seal with the endoscope shaft.

According to some embodiments of the invention, the endoscope cover lubricant port can be connected to a lubricant tube dispenser and the lubricant material can be injected into the lubricant port by squeezing the lubricant tube dispenser, such that at least part of the space between the inner sleeve and the outer sleeve is filled with lubricant material which also soaks the wiping material with lubricant material. At this stage, the endoscope may not be in contact with lubricant material. Alternatively, the wiping material can be soaked with the lubricant material before the wiping material is disposed within the outer sleeve.

After securing the sleeve proximal cuff, the endoscope sleeve can be changed from its compact format into its unpacked format. To achieve the unpacked state, the distal portion of the outer sleeve is pulled toward the distal portion of the endoscope shaft. This action disconnects the distal portion of the inner sleeve or other retainer from its connection to the distal portion of the outer sleeve. According to some embodiments, the retainer is at least one strap or ribbon. Once a portion of the retainer is disconnected from the outer sleeve, the outer sleeve can be pulled over the endoscope shaft toward the distal portion of the endoscope shaft. Simultaneously, the endoscope shaft can be lubricated evenly by the lubricant-soaked wiping material as the distal end of the endoscope cover moves along the length of endoscope shaft distally. Finally, the outer sleeve's distal end can be moved beyond the distal end of the endoscope shaft and the distal end of the outer sleeve can be closed using a zip lock mechanism or other closure mechanisms. The endoscope can then be transported to an examination room for a procedure.

Before using the endoscope, the closure mechanism at the distal end of the outer sleeve is opened. The outer sleeved is pulled over the endoscope shaft proximally until the distal end of the endoscope is out of the distal end of the outer sleeve. The distal end of the endoscope is already lubricated and can be inserted into a body cavity.

As the endoscope is further inserted into a body cavity, the outer sleeve is pulled over the endoscope shaft proximally. The endoscope shaft is grasped using wiping material supplied at the distal portion of the outer sleeve. At all times, the outer sleeve stays outside of the body cavity at the proximity of the body cavity opening. During the insertion of the endoscope into the body cavity, the outer sleeve's distal end portion is pulled over the endoscope shaft proximally to allow adequate exposure of the portion of the endoscope shaft that needs to be inserted into the body cavity. The lubricant material can be evenly distributed over the endoscope shaft by the wiping material. During the withdrawal of the endoscope from the body cavity, the outer sleeve is pulled over the endoscope shaft distally to cover the portion of the endoscope shaft that exits from the body cavity. The wiping material can absorb and clean the lubricant material and bodily fluid that is present over the endoscope shaft. After full removal of the endoscope from the body cavity, the outer sleeve can be extended beyond the endoscope tip. After covering the endoscope shaft in its entirety, the closure mechanism of the outer sleeve is sealed and the scope is ready for transportation back to the cleaning room. During endoscope insertion, the outer sleeve prevents all contact of the endoscope with any object in the examination room or with the hands of personnel, thereby reducing the likelihood of contamination of the endoscope shaft. During withdrawal, the outer sleeve prevents any potential contamination of any object or personnel in the examination room by the soiled endoscope.

Various implementations of the invention are shown and described herein with reference to the drawings. As depicted in FIG. 1, endoscope sleeve 10 of this invention is an endoscope accessory that can envelop an endoscope shaft and comprises at least one elongated, flexible, open-ended tubular sleeve, with a diameter larger than the diameter of an endoscope shaft. The sleeve 10 can removably receive an endoscope shaft in a loose slidable manner. Sleeve 10 can be substantially coaxially disposed with the endoscope shaft.

The endoscope sleeve 10 can be retained in a compact or shortened position. This can be achieved in various ways in accordance with the principles of the invention. The endoscope sleeve 10 can include a retainer, for example, a retainer disposed within the sleeve. The retainer can be any device or mechanism in accordance with the principles of the invention that maintains a portion of the sleeve in a compact format when at least a portion of the retainer is attached to the sleeve, and that allows the portion of the sleeve to achieve an unpacked or extended format when at least a portion of the retainer is detached from the sleeve. According to some embodiments, the retainer can be, for example, at least one of a second or inner sleeve, a strap, a ribbon, or a tab. According to some embodiments, the retainer can be a glue, a seal, or an adhesive. The retainer can be of the type that is releasable so when the unpacked or extended format is needed, the retainer can be released, disengaged or broken, for example.

Figure 2:
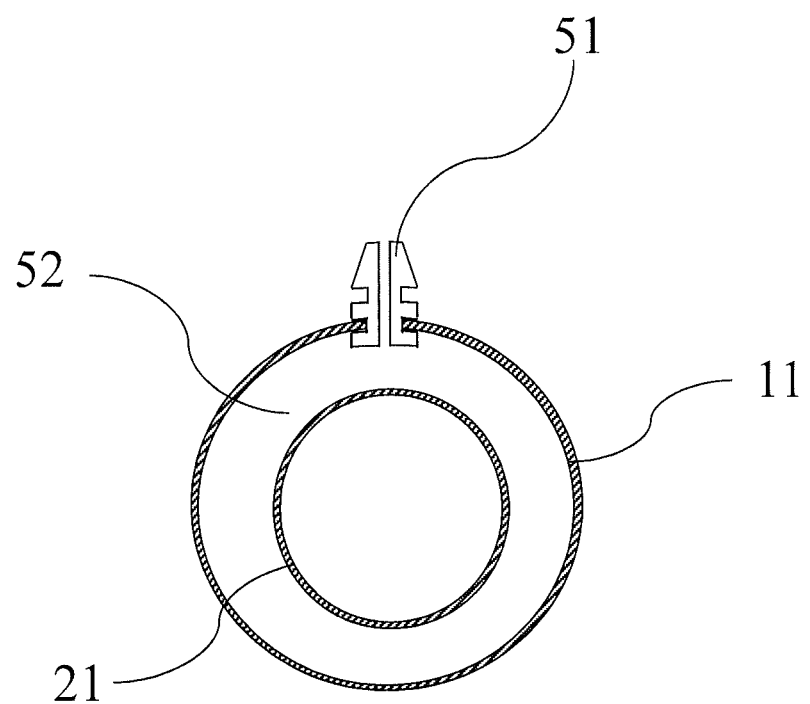
FIG. 2 is a cross sectional view taken along line A-A in FIG. 1 showing a lubricant port.

According to some embodiments, the retainer can be a second sleeve that is coaxial with the first sleeve. The endoscope sleeve 10 can thus be composed of two coaxial sleeves, the outer sleeve 11 and the inner sleeve 21, as depicted in FIG. 2. Inner sleeve 21 can have a length that is shorter than the length of the outer sleeve 11. The outer sleeve 11 terminates proximally at the proximal endoscope cover cuff 30. The proximal endoscope cover cuff 30 has a proximal opening 13. The outer sleeve 11 has a midportion 14 and a distal end portion 15 that can be supplied with a lubricant port 51 and that has a distal opening 16 that can be closed using a closure mechanism 17.

Figure 17:
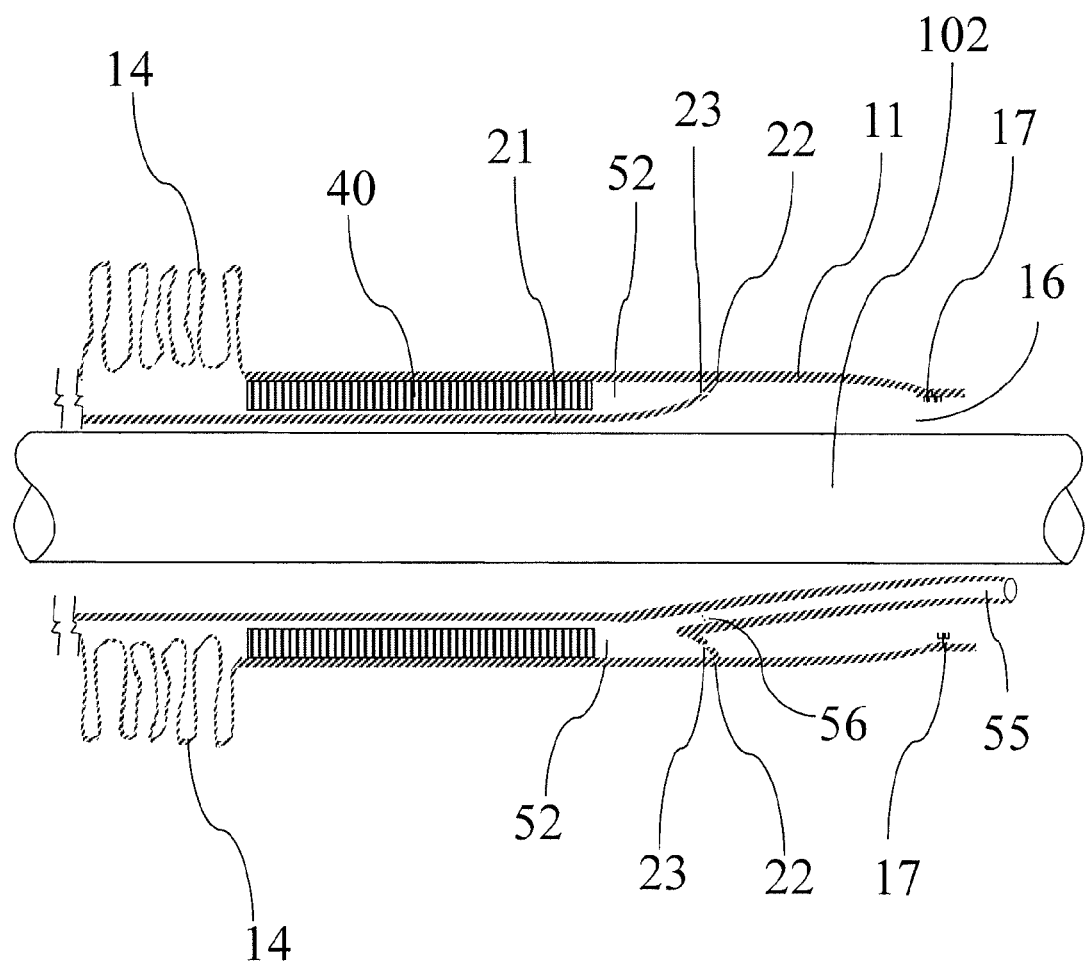
FIG. 17 is a partial cross-sectional view taken along section C-C in FIG. 1 when the outer sleeve is in the compact configuration and when the outer sleeve distal end is open, and shows an alternative embodiment in accordance with the principles of the invention.

As depicted in FIG. 2, according to some embodiments of the invention, the distal end portion 15 of the outer sleeve 11 can be supplied with a lubricant port 51. The lubricant port 51 can be used to introduce a lubricant material into the space 52 between the outer sleeve 11 and the retainer 21, as in the case when the retainer 21 is a second sleeve. In this case, the lubricant port can be connected to the outer sleeve 11, the inner sleeve 21, or can be at the junction between the inner sleeve 21 and the outer sleeve 11. According to some embodiments, the inner sleeve 21 can have a reservoir within it that can be filled with lubricant, and that can be used to discharge lubricant. In the case that the retainer 21 is a strap, a ribbon, a tab, or another type of retainer, the lubricant port 51 may be used to introduce a lubricant material into the outer sleeve 11 surrounding the endoscope. Alternatively, the lubricant port may be connected to the retainer 21. The lubricant port may be used to fill a reservoir within the retainer 21, as shown in FIG. 17.

Figure 3:
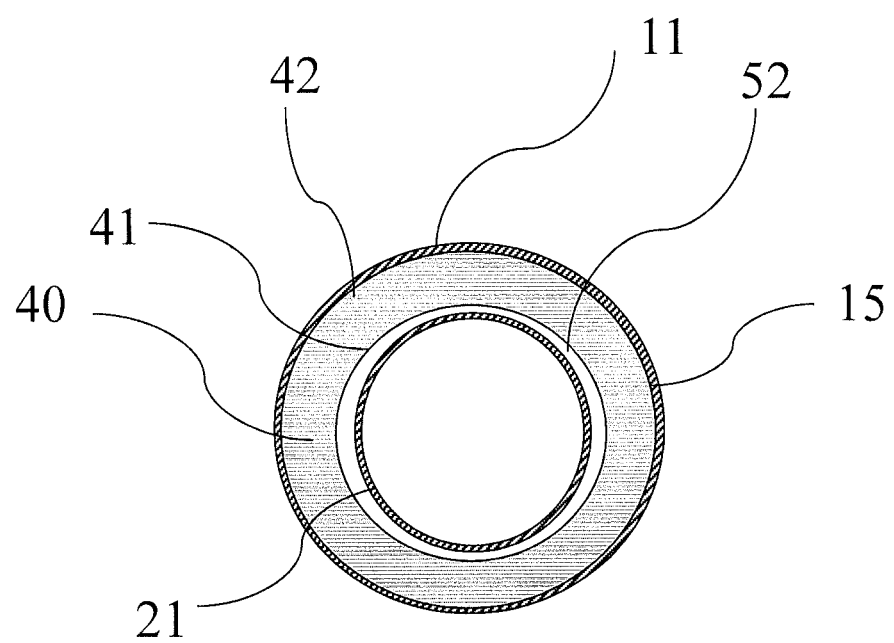
FIG. 3 is a cross sectional view taken along line B-B in FIG. 1.

According to some embodiments of the invention, as depicted in FIG. 3, the interior surface at the distal end portion 15 of the outer sleeve 11 can be supplied with at least one wiping material 40 disposed within the space 52 between the inner sleeve 21 and the outer sleeve 11 distal end portion 15. According to some embodiments, the wiping material 40 is an elongated, flexible, open-ended tubular wiping material. The wiping material 40 has an interior surface 41 and an exterior surface 42. The exterior surface 42 of the tubular wiping material 40 can be adhered to the interior surface of the outer sleeve 11 at the distal end portion 15.

Figure 4:
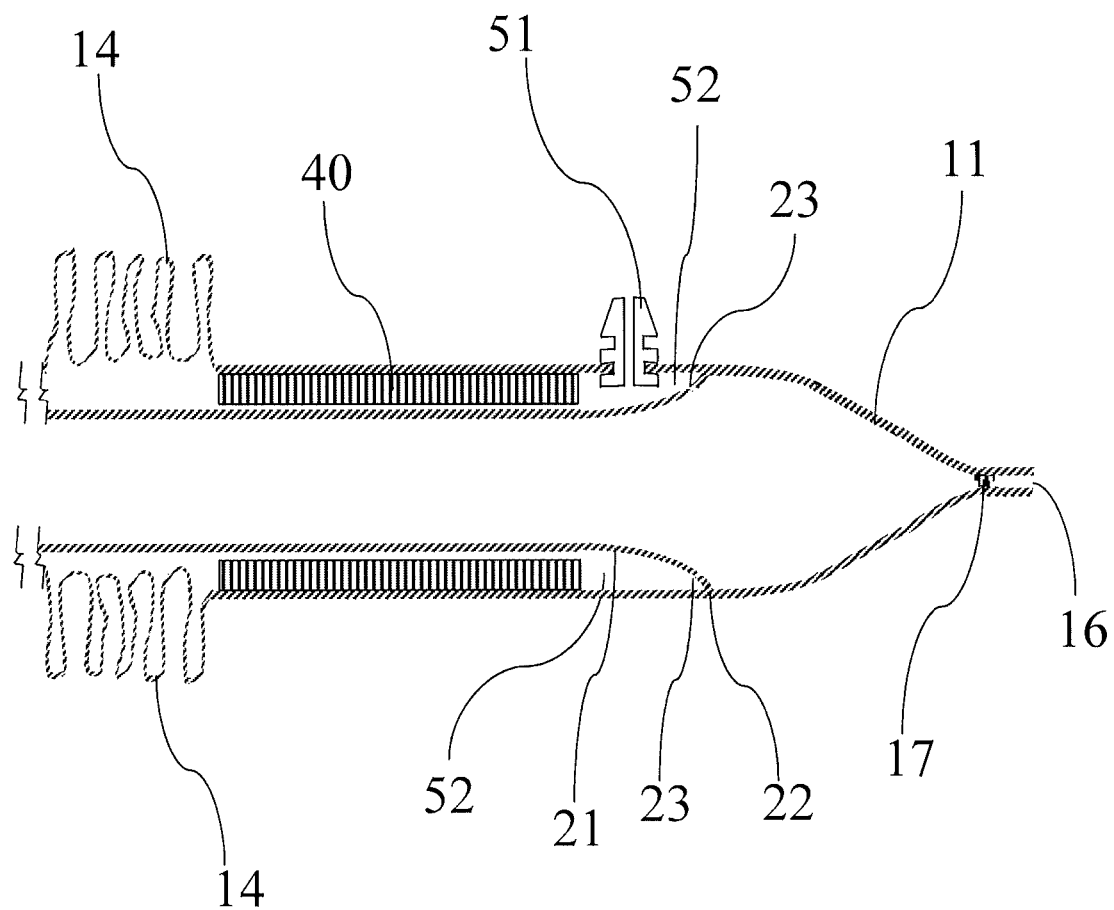
FIG. 4 is a partial longitudinal sectional view taken along line C-C in FIG. 1 and showing a tubular wiping material and a lubricant port.

FIG. 4 also shows the distal end portion the endoscope cover 10 in its compact format. In this view, the distal end portion 15 of the outer sleeve 11 is supplied with at least one elongated, flexible, open-ended tubular wiping material 40, within the space 52 between the inner sleeve 21 and the outer sleeve 11 distal end portion 15. The wiping material 40 has an interior surface 41 and an exterior surface 42. The exterior surface 42 of the tubular wiping material 40 can be adhered to the interior surface of the outer sleeve 11 at the distal end portion 15. The distal end portion of the outer sleeve can also be supplied with a lubricant port 51 that can be used to fill the space 52 with lubricant material. The lubricant port 51 can be positioned near the distal end of the cavity 52, or in another position, such as over the wiping material 40, for example. The lubricant port can have a variety of different forms. The lubricant port can be made from a small flexible tubular projection 55 (shown in FIG. 17) that is connected to the cavity 52 as a projection to the inner sleeve 21. According to some embodiments, the tubular projection 55 extends beyond the distal end 16 of the outer sleeve 11 to allow the cavity 52 to be filled with lubricant. The tubular projection 55 can be pushed inside the sleeve 11 after being used or can be torn away along a perforated line 56 at its base if it is not needed after use. The tubular projection 55 can also be closed with a zip lock or tie down closure. Alternatively the lubricant port can be a button, for example. The lubricant port can be made from a one way valve placed on the outer sleeve or on the inner sleeve. The lubricant can be injected into the reservoir using a syringe that can be connected to the variety of ports mentioned above or through a needle directly into the inner sleeve 21 or outer sleeve 11. According to some embodiments, the wiping material 40 can be pre-soaked with the lubricant, and the outer sleeve can be provided with or without the lubricant port 51 or other varieties of the port mentioned above.

The distal end portion 15 of the outer sleeve 11 also has a distal opening 16 that can be closed using the closure mechanism 17. The inner sleeve 21 distally has an end portion 22 that connects to the outer sleeve 11 internal surface. The inner sleeve 21 can be disconnected from its end portion 22 along a perforated line 23. The inner sleeve 21 thus acts as a retainer that maintains a portion of the outer sleeve in a compact configuration. According to some embodiments, the retainer 21 has a different form, such as a strap, a ribbon, or a tab. A portion of the retainer 21 can be removably attached to the outer sleeve 11 which, according to some embodiments, is the only sleeve. One or more straps, ribbons, or tabs, or a combination thereof, can be used to maintain a portion of the outer sleeve 11 in a compact configuration when the detachable portion of the retainer 21 is attached to the at least one flexible sleeve 11.

Figure 5:
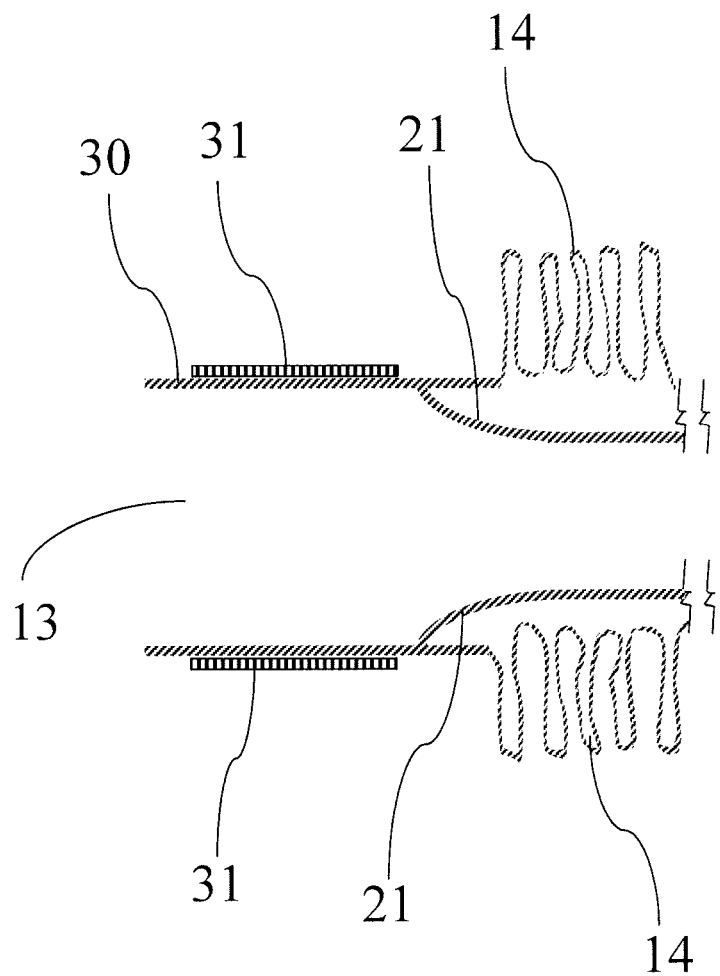
FIG. 5 is a partial longitudinal sectional view taken along line D-D in FIG. 1 and showing the proximal end of the endoscope sleeve.

As depicted in FIGS. 5, the midportion 14 of the outer sleeve 11 can be connected proximally with the endoscope cover proximal cuff 30 which is provided with the endoscope shaft seal mechanism 31 that removably secures the proximal cuff 30 to an endoscope shaft or its proximal junction to the endoscope control knob. The endoscope shaft seal mechanism 31 may be fabricated from an elastomeric material, self-fusing silicon tape, purse string closure, tie-on closure, pressure sensitive adhesive tape, or other similar material or a combination thereof. Alternatively, the proximal cuff 30 can be supplied with other securing mechanisms such as a hook-and-loop fastener, a purse string closure or a tie-on closure on the exterior surface of the proximal cuff 30 (not shown). Alternatively, the proximal cuff 30 may be configured to have a band of pressure sensitive adhesive with a release sheet on the interior surface that can be adhered to the proximal portion of an the endoscope shaft or the graduated, conical endoscope junction after removal of the release sheet (not shown in the figures).

Figure 6:
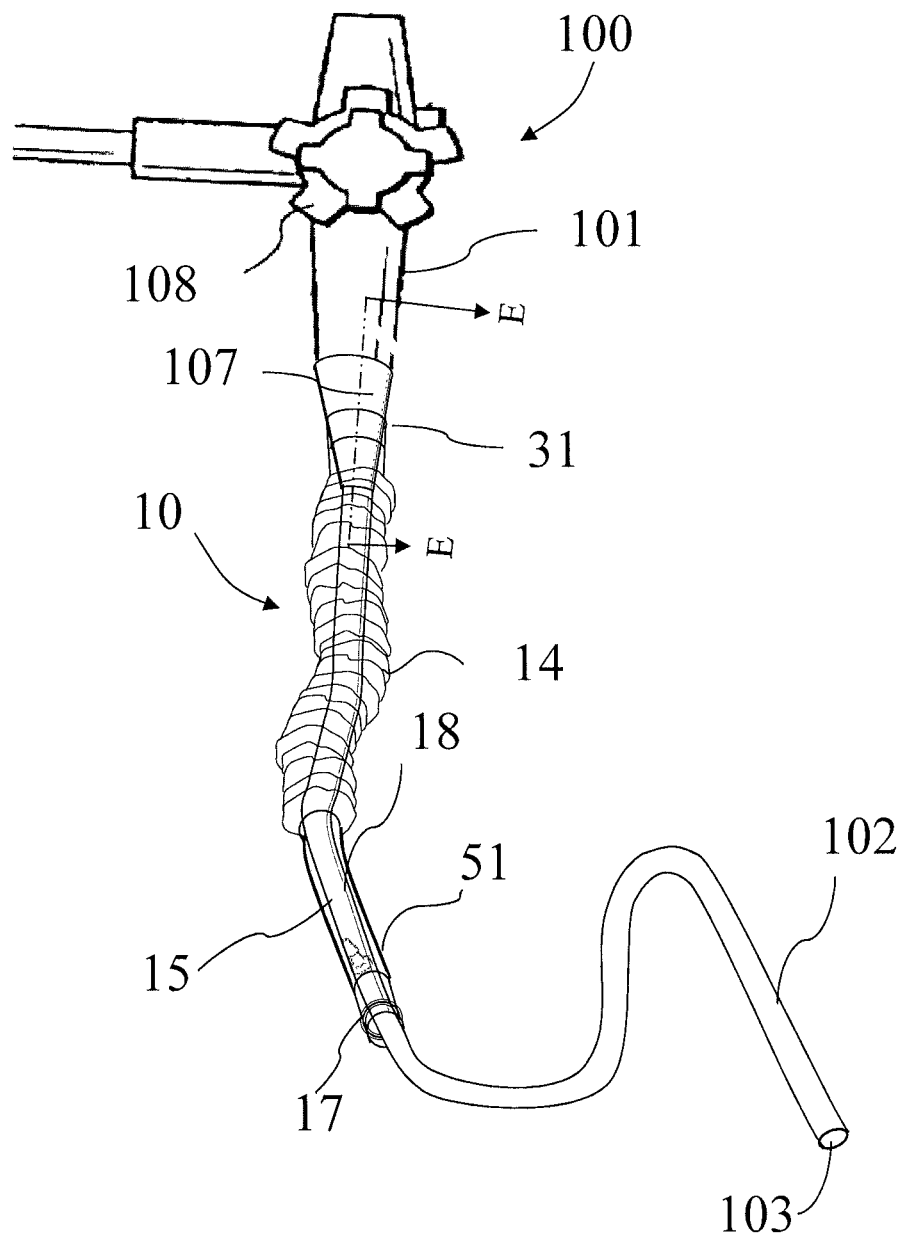
FIG. 6 is a schematic illustration showing the endoscope sleeve in the compact format mounted over the shaft of an endoscope with the proximal end of the endoscope sleeve fitted over the proximal conical portion of the endoscope shaft.

As depicted in FIG. 6, the endoscope 100 comprises an endoscope knob portion 101 and an endoscope shaft 102. The endoscope knob 108 is located on the endoscope knob portion 101. The endoscope knob portion 101 is connected to the endoscope shaft 102 in a graduated endoscope junction 107, also referred to as a conical connection 107. The endoscope shaft 102 ends distally at an endoscope tip 103. The endoscope sleeve 10 can be provided with a line of weakness 18 along the entire length of the tube that can be used to tear open the outer and/or inner sleeve for removal of the endoscope shaft 102 out of the endoscope sleeve 10 in a sideways, partial or complete manner.

Figure 7:
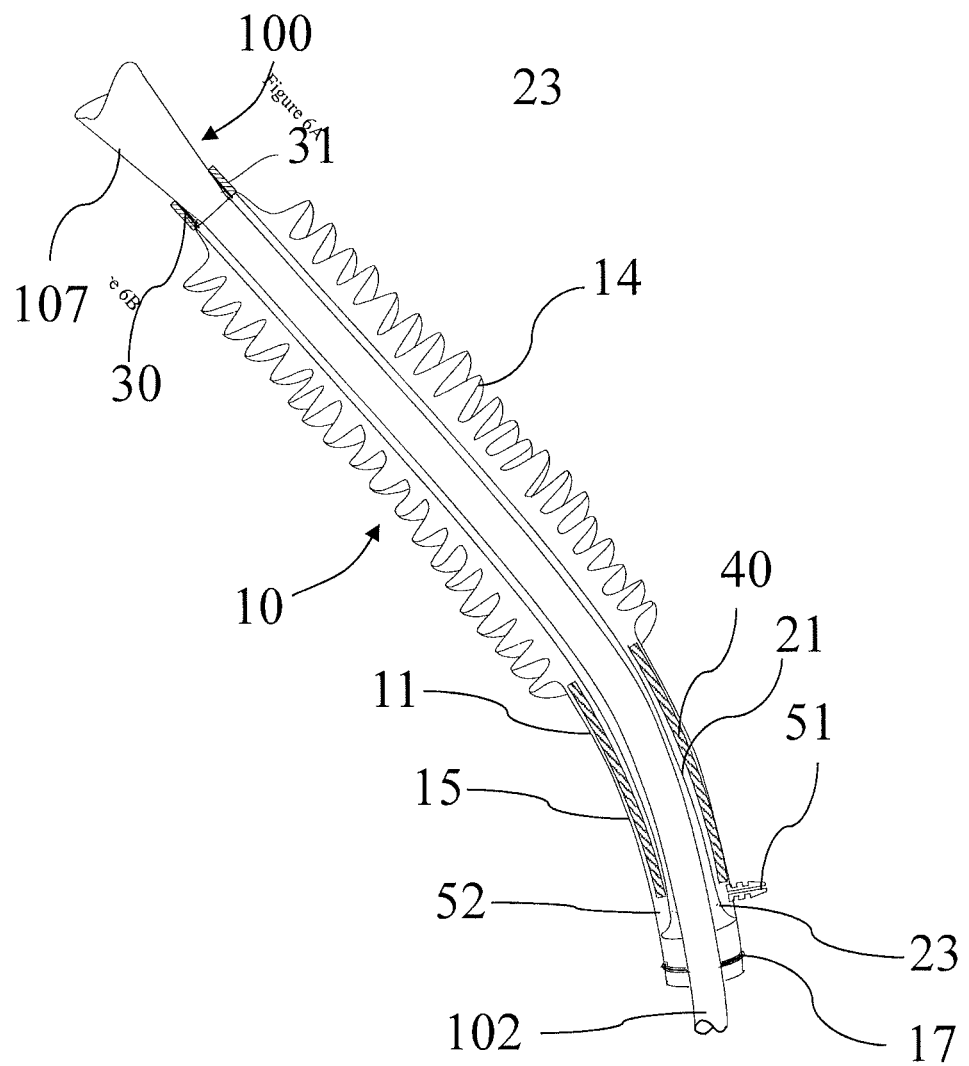
FIG. 7 is a partial longitudinal sectional view showing the endoscope sleeve in the compact format mounted over the shaft of an endoscope with the proximal end of the endoscope sleeve fitted over the proximal conical portion of the endoscope shaft.

As depicted in FIG. 7, the midportion 14 of the outer sleeve 11 is connected proximally with the endoscope cover proximal cuff 30 which is provided with the endoscope shaft seal mechanism 31 that removably secures the proximal cuff 30 to an endoscope shaft 102 or its graduated endoscope junction 107. According to some embodiments, the outer sleeve 11 distal end portion 15 is supplied with at least one wiping material 40 within the space 52 between the inner sleeve 21 and the outer sleeve 11 distal end portion 15. In embodiments that do not include the inner sleeve 21, the wiping material can be disposed within the outer sleeve 11. The wiping material can have a tubular form that is co-axial with the outer sleeve. The tubular wiping material can circumscribe the endoscope when the endoscope is inserted into the outer sleeve. The wiping material can also have a rectangular or other form that does not fully circumscribe the endoscope. The wiping material can be multiple. The distal end portion of the outer sleeve can be supplied with a lubricant port 51 that can be used to fill the space 52 with lubricant material. The distal end portion 15 of the outer sleeve 11 can also have a closure mechanism 17.

Figure 8:
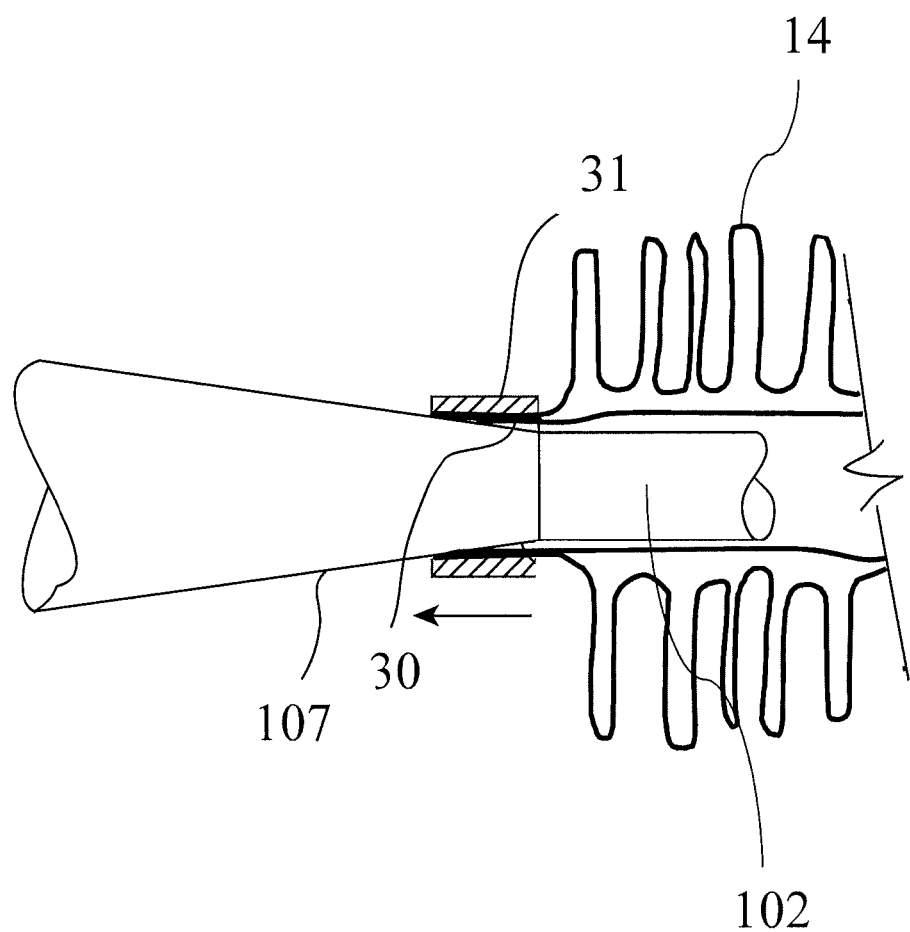
FIG. 8 is a partial longitudinal sectional view taken along line E-E in FIG. 6 and showing the proximal end of the endoscope sleeve.

As depicted in FIG. 8, the midportion 14 of the outer sleeve 11 can be connected proximally with the proximal cuff 30 which is provided with the endoscope shaft seal mechanism 31 that removably secures the proximal cuff 30 to an endoscope shaft 102 or its graduated endoscope junction 107.

Figure 9:
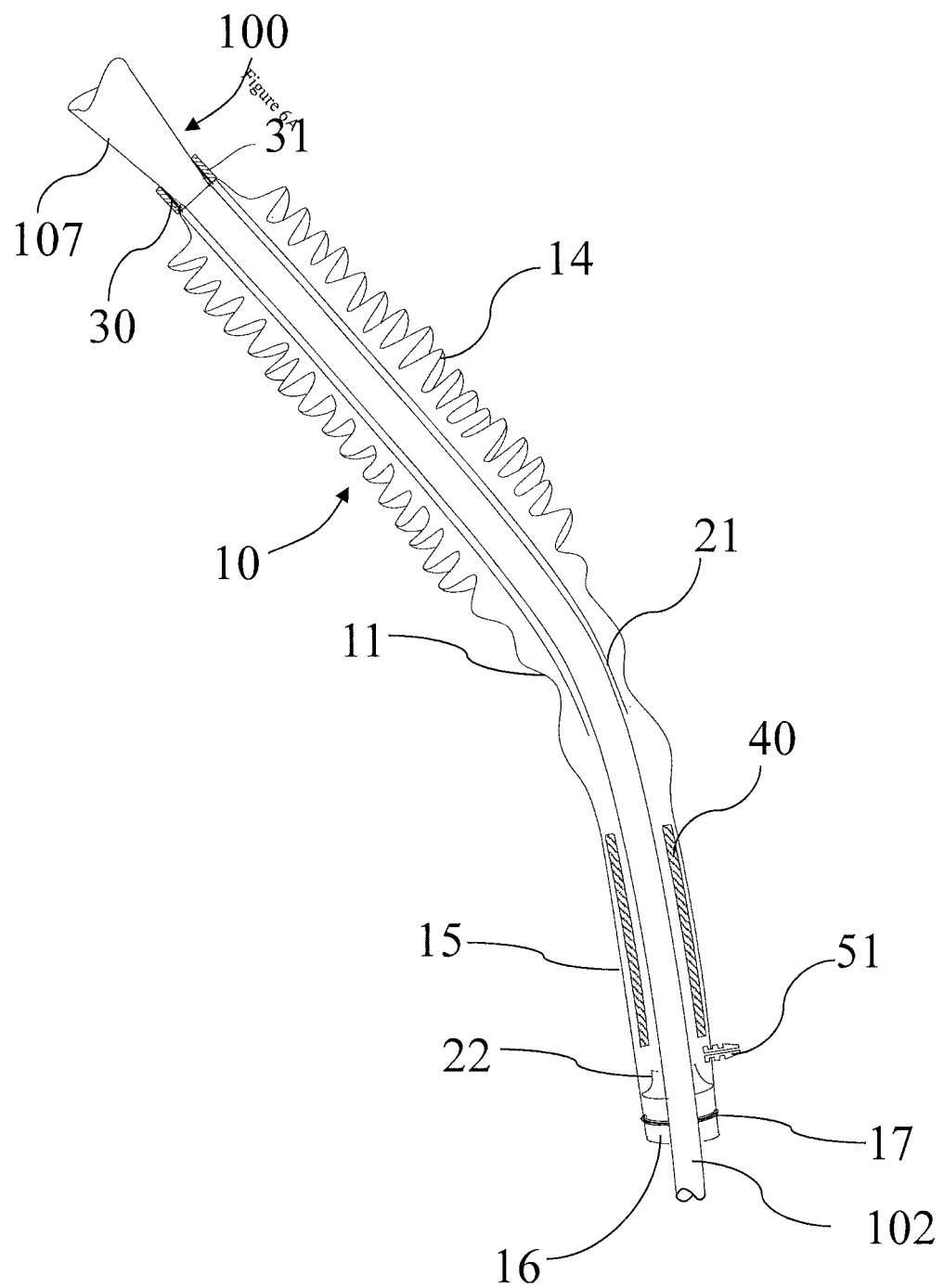
FIG. 9 is a partial longitudinal sectional view showing the endoscope sleeve transition from the compact to the unpacked format over the shaft of an endoscope with the proximal end of the endoscope sleeve fitted over the proximal conical portion of the endoscope shaft.

As depicted in FIG. 9, the midportion 14 of the outer sleeve 11 is connected proximally with the proximal cuff 30 which is provided with the endoscope shaft seal mechanism 31 that removably secures the proximal cuff 30 to the endoscope shaft 102 or its graduated endoscope junction 107. According to some embodiments of the invention, the distal end portion 15 of the outer sleeve 11 can be supplied with the wiping material 40 within the space 52 between the inner sleeve 21 and the outer sleeve 11. The distal end portion of the outer sleeve is also supplied with a lubricant port 51 that can be used to fill the space 52 with lubricant material. The distal end portion 15 of the outer sleeve 11 also has the closure mechanism 17.

After securing the sleeve proximal cuff 30, the endoscope sleeve 10 can be changed from its compact format into its unpacked format as shown in FIG. 9. In order to accomplish this, the distal portion 15 of the outer sleeve 11 is pulled towards the distal portion of the endoscope shaft 102. By doing this a portion of the retainer 21 can be disconnected from the outer sleeve 11. For example, the retainer can have a perforated line 23 along which the portion of the retainer becomes disconnected from the outer sleeve 11. The perforated line 23 can be at a distal portion of the retainer 21 such that the distal portion of the retainer 21 detaches from the outer sleeve 11 while the proximal portion of the retainer 21 remains attached to the outer sleeve 11. According to some embodiments of the invention, the proximal portion of the retainer 21 is attached to the proximal portion of the outer sleeve 11, and the distal portion of the retainer 21 is removably attached to the distal portion of the outer sleeve 11. Alternatively, according to some embodiments, the proximal portion of the retainer 21 is attached to the proximal portion of the outer sleeve 11, and the distal portion of the retainer 21 is removably attached to the midportion of the outer sleeve 11. When the portion of the retainer 21 becomes disconnected from the outer sleeve 11, a small portion 22 of the retainer 21 may remain connected to the outer sleeve 11.

Once the portion of the retainer 21 has been detached from the outer sleevel 1, the outer sleeve 11 can be pulled over the endoscope shaft 102 toward distal portion of the endoscope shaft 102. When the outer sleeve 11 covers the endoscope shaft 102 in its entirety, the distal end of the outer sleeve 16 is closed using the zip lock or other closure mechanisms 17.

Figure 10:
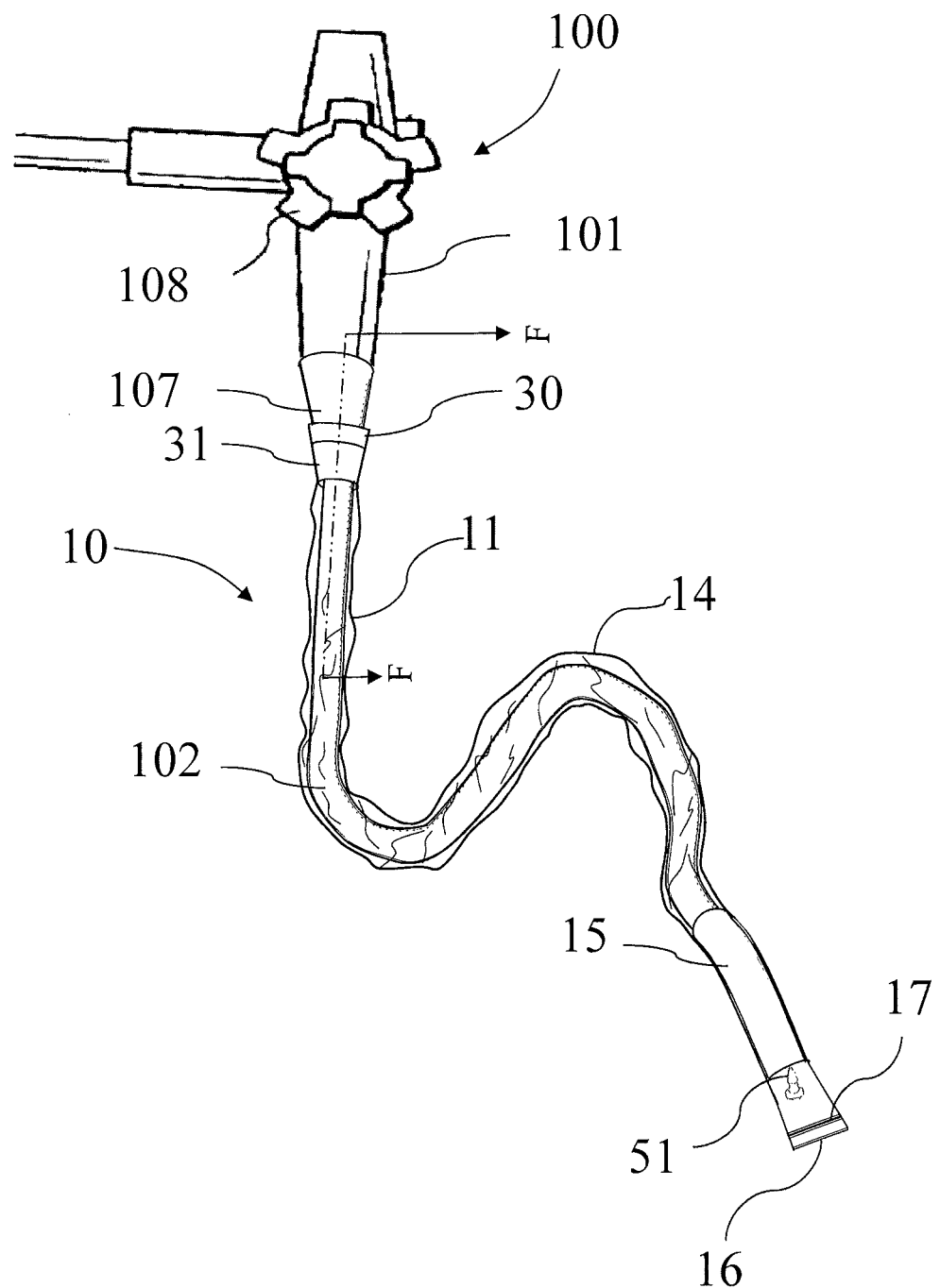
FIG. 10 is a schematic illustration showing the endoscope sleeve in the unpacked format mounted over the shaft of an endoscope with the proximal end of the endoscope sleeve fitted over the proximal conical portion of the endoscope shaft and the distal end of the endoscope sleep extends beyond the distal end of the endoscope.

As depicted in FIG. 10, the outer sleeve 11, in its unpacked format, can cover the endoscope shaft 102 in its entirety. In this format, the sleeve proximal cuff 30 is secured to the endoscope shaft 102 or its graduated endoscope junction 107, the midportion 14 of the outer sleeve 11 covers the endoscope shaft 102 and the distal end 16 of the outer sleeve 11 is closed using the zip lock or other closure mechanisms 17.

Figure 11:
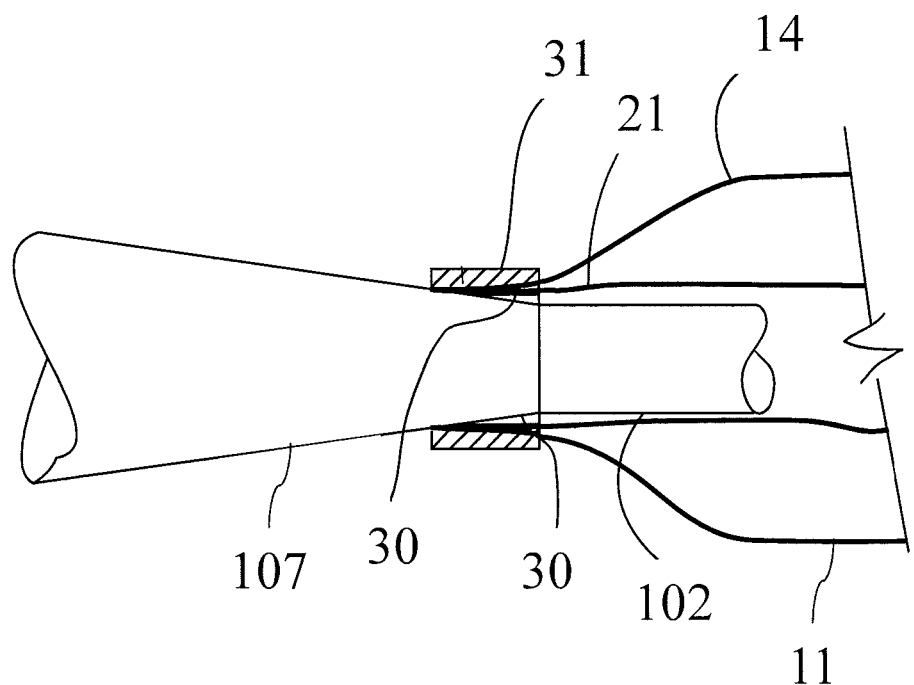
FIG. 11 is a partial longitudinal sectional view taken along line F-F in FIG. 10 and showing the proximal end of the endoscope sleeve.

As depicted in FIG. 11, the outer sleeve 11, in its unpacked format, can be connected proximally with the endoscope cover proximal cuff 30 which is provided with the endoscope shaft seal mechanism 31 that removably secures the proximal cuff 30 to an endoscope shaft 102 or its graduated endoscope junction 107.

Figure 12:
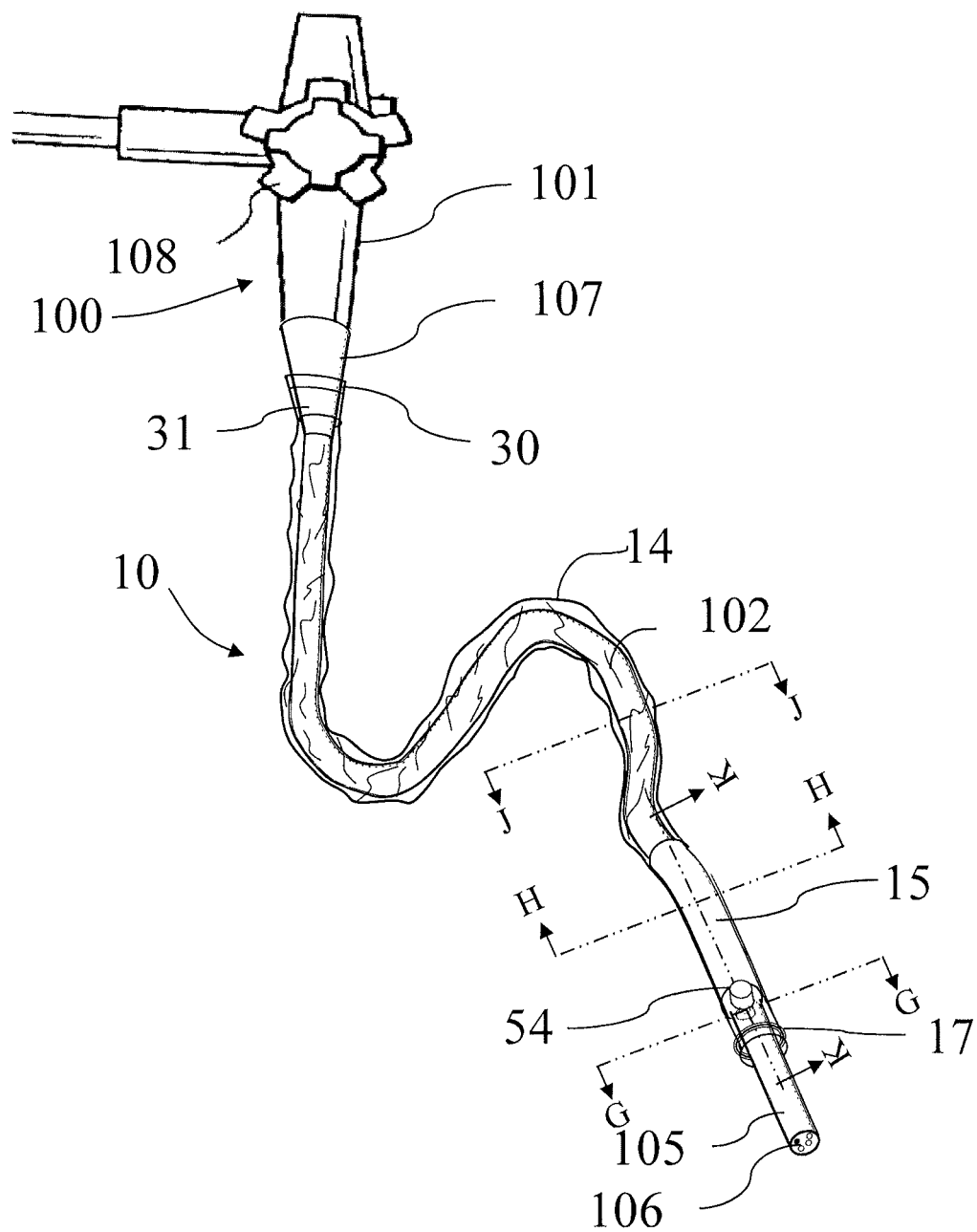
FIG. 12 is a schematic illustration showing the endoscope sleeve in the unpacked format mounted over the shaft of an endoscope with the proximal end of the endoscope sleeve fitted over the proximal conical portion of the endoscope shaft and the distal end of the endoscope sleeve pulled back to allow the distal end of the endoscope to go beyond the distal end of endoscope sleeve.

As depicted in FIG. 12, the closure mechanisms 17 at the distal end portion 15 of the outer sleeve 11 in its unpacked format can be opened and the distal end 15 can be pulled proximally over the endoscope shaft 102 to expose the distal shaft portion 105 and the distal end 106 of the endoscope just before the insertion of the distal end 106 into a body cavity. For this purpose, the distal end portion 15 of the outer sleeve 11 is held loosely and moved in a slidable manner over the endoscope shaft 102 to expose the distal end 106 of the endoscope shaft 102 beyond the distal opening 16 of the outer sleeve 11. While the distal end portion 15 of the outer sleeve 11 is retracted over the endoscope shaft, the midportion 14 of the outer sleeve 11 can be pleated over the endoscope shaft 102 as the shaft is further distally exposed. Then the distal end portion 15 of the outer sleeve 11 is firmly grasped so the distal end 106 of the endoscope can be inserted into a body cavity. After inserting the distal end 106 of the endoscope into the body cavity, the grasp on the distal end portion 15 of the outer sleeve 11 can be loosened and the distal end portion 15 of the outer sleeve 11 can be further retracted over the endoscope shaft 102 to expose a few more inches of the endoscope shaft 102. Then the exposed portion of the endoscope shaft 102 can be pushed further into body cavity. This sequence can be repeated during insertion of the endoscope into the body cavity.

Figure 13:
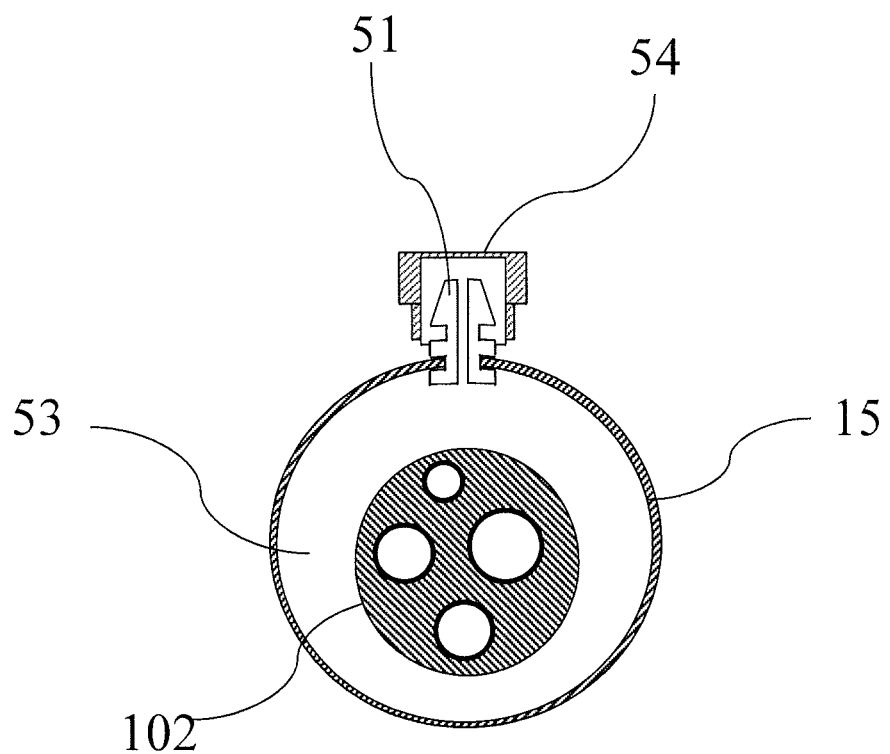
FIG. 13 is a cross sectional view of the endoscope sleeve and the endoscope taken along line G-G in FIG. 12 showing a lubricant port.

As depicted in FIG. 13, according to some embodiments of the invention, the distal end portion 15 of the outer sleeve 11 in its unpacked format can be supplied with a lubricant port 51 that can be capped with lubricant port cap 54. The lubricant port can be used to fill the space 53 between the outer sleeve 11 and endoscope shaft 102 with lubricant material.

Figure 14:
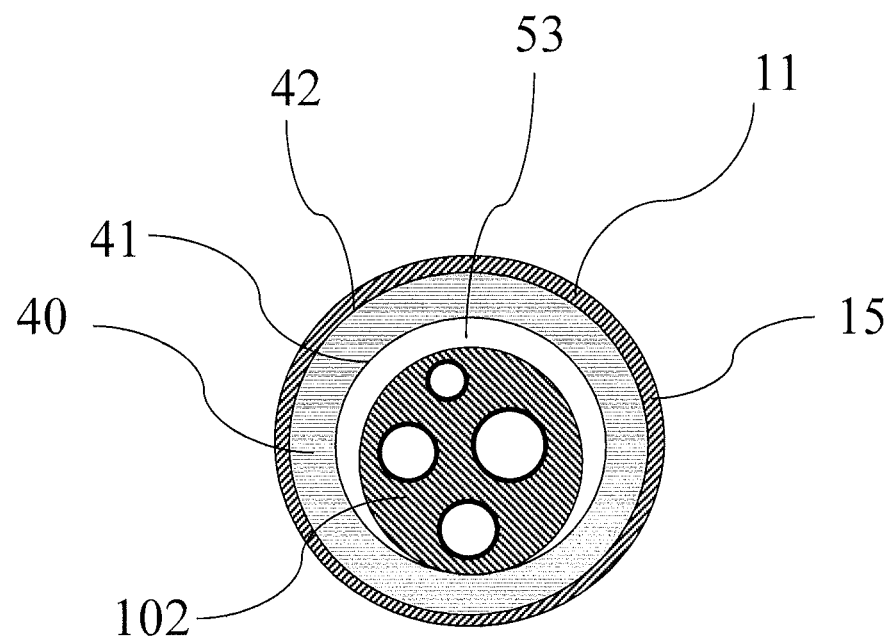
FIG. 14 is a cross sectional view of the endoscope sleeve and the endoscope taken along line H-H in FIG. 12 and showing a tubular wiping material.

As depicted in FIG. 14, according to some embodiments of the invention, the interior surface at the distal end portion 15 of the outer sleeve 11 in its unpacked format can be supplied with at least one elongated, flexible, open-ended tubular wiping material 40, within the space 53 between the outer sleeve 11 and the endoscope shaft 102. The wiping material 40 having an interior surface 41 and an exterior surface 42. The exterior surface 42 of the tubular wiping material 40 is adhered to the interior surface at the distal end portion 15 of the outer sleeve 11.

Figure 15:
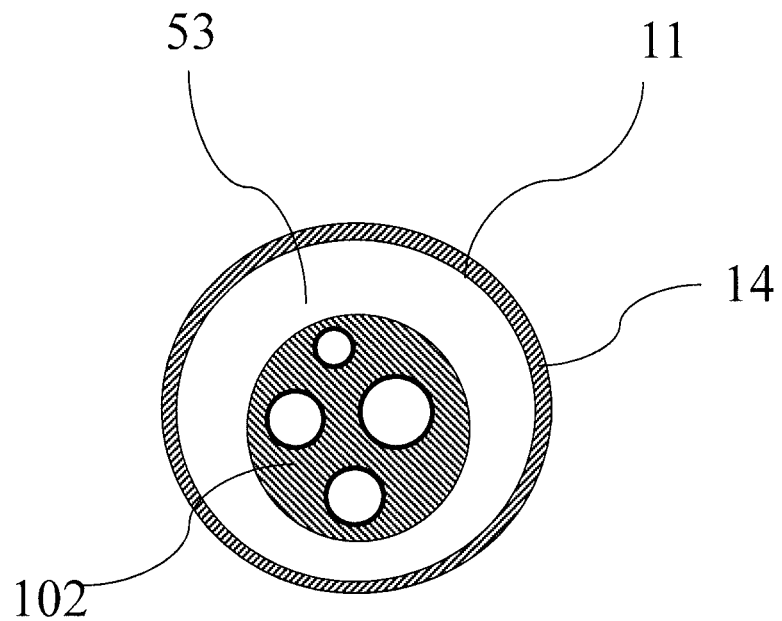
FIG. 15 is a cross sectional view of the endoscope sleeve and the endoscope taken along line J-J in FIG. 12.

As depicted in FIG. 15, the midportion 14 of the outer sleeve 11 in its unpacked format covers the endoscope shaft 102.

Figure 16:
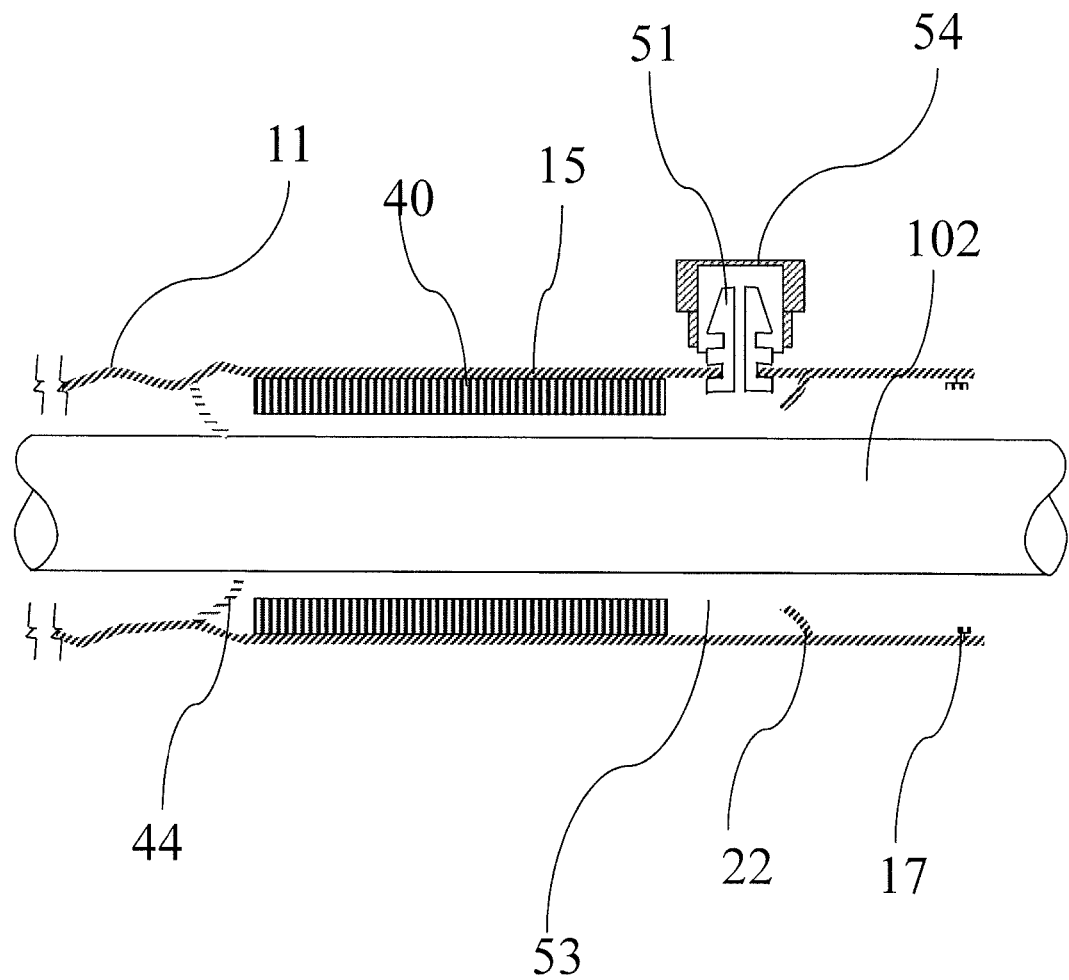
FIG. 16 is a partial longitudinal sectional view of the endoscope sleeve and the endoscope taken along line K-K in FIG. 12 and showing the distal end of the endoscope sleeve.

As depicted in FIG. 16, the distal end portion 15 of the outer sleeve 11 in its unpacked format can be supplied with an elongated, flexible, open-ended tubular wiping material 40, within the space 53 between the outer sleeve 11 and the endoscope shaft 102, and can be supplied with a lubricant port 51 that can be capped with lubricant port cap 54. The lubricant port can be used to fill the space 53 between the outer sleeve 11 and endoscope shaft 102 with lubricant material. The distal portion of the retainer 21 may disconnect from the outer sleeve 11 by perforating along a line in the distal portion of the retainer 21. After disconnecting from the outer sleeve along the perforated line 23, a small portion 22 may still be connected to the internal surface of the outer sleeve 11.

In another optional embodiment of this invention, as depicted in FIG. 16, the distal end portion 15 of the outer sleeve 11 can be equipped with at lease one annular squeegee 44 on the interior surface of outer sleeve 11. Annular squeegee/s 44 can be composed of a donut shaped rubbery protrusion with an inner and outer ring. The outer ring can be attached to the interior surface of the outer sleeve 11 at the distal end portion 15 of the outer sleeve 11 and the squeegee 44 can be positioned at an angle to the axis of the distal end portion of the outer sleeve 11, as shown. The inner ring diameter of annular squeegee 44 can be sized as such that the inner ring creates loose, circumferential contact over the endoscope shaft 102 surface. The angle, shape, and material properties of annular squeegee 44 can be configured to provide a low friction interface over the endoscope shaft 102 surface to provides a way for cleaning the endoscope shaft 102 surface when the distal end portion 15 of the outer sleeve 11 is moved over the endoscope shaft 102.

The distal end portion 15 of the outer sleeve 11 may be molded or cast from an elastomeric material such as silcone rubber or urethane rubber, or a non-elastomeric material supplied with one or all three components of tubular wiping material 40, annular squeegee 44, and lubricant dispenser 51 in the configuration shown, or in a similar configuration.

The midportion 14 of the outer sleeve 11 is configured to create minimal friction between the interior surface of the outer sleeve 11 and surface of the endoscope shaft 102 and can be reversibly pleated over the endoscope shaft 102.

The forgoing description and the drawings are illustrative of the invention and are not intended as limitations. Still other variants and rearrangements of structural parts are possible without departing from the spirit and scope of this invention and will readily present themselves to those skilled in the art.

In use, the endoscope sleeve 10 is mounted over the endoscope shaft 102. This can be performed in an endoscope cleaning room before transporting the endoscope 100 to the examination room. For mounting the endoscope sleeve 10 over the endoscope shaft 102, the proximal opening 13 of the endoscope sleeve 10 is pulled over the endoscope tip 106 and the sealing collar 30 is pulled along the endoscope shaft 102 proximally until the proximal opening 13 of the endoscope sleeve 10 reaches the proximal portion of the endoscope shaft 102 or the graduated endoscope junction 107. Then, the sealing collar 30 of the endoscope sleeve 10 is secured to the proximal portion of the endoscope shaft 102 or the graduated endoscope junction 107.

According to some embodiments of the invention, a lubricant material can be introduced into the endoscope sleeve using at least one of the lubricant injection ports. To do this, the lubricant port cap 54 is removed from the port 51 to open the said port on the distal end portion of the outer sleeve. The port is connected to a lubricant dispenser and lubricant is injected through the port 51 to fill the space 52 between the outer sleeve 11 and the inner sleeve 21 with lubricant material. Alternatively, the port 51 can be used to inject lubricant material into the space 53. Alternatively, other ports such as port 55 can be used to fill the space 52 with lubricant material and after use the port can be pushed inside the sleeve 11 or it can be removed by tearing along a perforated line 56.

According to some embodiments of the invention, once the sealing collar 30 of the endoscope sleeve 10 is secured to the proximal portion of the endoscope shaft 102 or the graduated endoscope junction 107, the endoscope sleeve 10 can be changed from its compact format into its unpacked format. To do this, the distal portion 15 of the outer sleeve 11 is pulled toward the distal portion of the endoscope shaft 102. With this action, the distal portion of the retainer shown as sleeve 21, can be disconnected from the outer sleeve 11 along a perforated line 23. Then the outer sleeve 11 is pulled over the endoscope shaft 102 toward the distal portion of the endoscope shaft 102. The length of outer sleeve 11 is sized so that after securing the endoscope shaft seal 30 at the proximal portion of the endoscope shaft 102 or the graduated endoscope junction 107, the distal opening 16 of the outer sleeve 11 can extend beyond the distal end 106 of the endoscope. When the outer sleeve covers the endoscope shaft 102 in its entirety, the distal end of the outer sleeve 16 is closed using the zip lock or other closure mechanisms 17. During this process the space 52 opens up and the lubricant material is now present between the outer sleeve 11 and endoscope shaft 102 in space 53. The endoscope shaft 102 is evenly lubricated with wiping material that moves distally over the shaft of endoscope 102.

The scope is transferred to the examination room for performing the procedure. Just prior to insertion of the endoscope shaft into the patient's body cavity, the closure mechanisms 17 at the distal end portion 15 of the outer sleeve 11 in its unpacked format is opened and the outer sleeve 11 distal end 15 can be pulled proximally over the endoscope shaft 102 to expose the distal portion 105 of the endoscope shaft and the distal end 106 of the endoscope is exposed. For this purpose, the distal portion 15 of the outer sleeve 11 is held loosely and moved in a slidable manner over the endoscope shaft 102 to expose the distal end 106 of the endoscope beyond the distal opening 16 of the endoscope outer sleeve 11. While the distal end portion 15 of the outer sleeve 11 is retracted over the endoscope shaft, the midportion 14 of the outer sleeve 11 can be pleated over the endoscope shaft 102 as the shaft is further exposed distally. Then the distal end portion 15 of the outer sleeve 11 is firmly grasped so the distal end 106 of the endoscope can be inserted into a body cavity. After inserting the endoscope shaft into the body cavity, the grasp on the distal end portion 15 of the outer sleeve 11 is loosened and the distal end portion 15 of the outer sleeve 11 is further retracted over the shaft of endoscope 102 to expose a few more inches of the endoscope shaft 102. Afterwards, the exposed portion of the endoscope shaft 102 can be further pushed into body cavity. This sequence can be repeated during insertion of the endoscope into the body cavity.

The distal end portion 15 of the outer sleeve 11 stays at the proximity but outside of the body cavity opening at all times.

During withdrawal of endoscope shaft 102 from the body cavity, the sequence that is mentioned above can be reversed. The distal end portion 15 of the outer sleeve 11 is firmly grasped to pull the endoscope shaft 102 a few inches out of the body cavity. Then the distal end portion 15 of the outer sleeve 11 is loosely grasped and moved forward in a loose slidable fashion over the endoscope shaft 102 to cover the exposed portion of the endoscope shaft 102. This sequence is repeated during withdrawal of the endoscope out of the body cavity until the distal end 106 of the endoscope is out of the body cavity. Then, the distal end portion 15 of the outer sleeve 11 is pulled over and beyond the distal end 106 of the endoscope and the closure mechanism 17 is closed.

The endoscope 100 can then be transported to the endoscope cleaning room for the cleaning process while the endoscope shaft 102 is completely enclosed in outer sleeve 11.

To remove the endoscope sleeve 10 from the endoscope 100, the sealing collar 30 can be opened and the endoscope shaft 102 can be pulled out of the endoscope sleeve 10. Alternatively, the sleeve 10 can be opened along a line of weakness 18 extending from the proximal end to the distal end, and the endoscope shaft 102 can be removed out of sleeve 10 in a sideways manner.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

I claim:

1. An endoscope sleeve comprising:
a sleeve defining a lumen for accepting an endoscope in a slidable manner, the sleeve having a proximal end configured to accept the endoscope and a distal end configured to be slidably disposed over the endoscope, wherein the sleeve comprises a compact configuration and an extended configuration; and
a retainer configured to be detachably attached to the sleeve, wherein in the compact configuration the retainer is attached to the sleeve and in the extended configuration the retainer is detached from the sleeve allowing the sleeve to be extendable over the endoscope,
wherein the sleeve comprises a first sleeve and the retainer comprises a second sleeve, and the second sleeve defines the lumen for accepting the endoscope,
wherein the second sleeve has a length that is less than a length of the first sleeve, and
wherein the first sleeve and the second sleeve define a cavity therebetween.

2. The endoscope sleeve of claim 1, wherein the proximal end of the sleeve includes a collar configured to secure the sleeve to the endoscope.

3. The endoscope sleeve of claim 2, wherein the proximal end of the sleeve further comprises a sealing mechanism to seal the collar to the endoscope with a reversible, liquid-tight seal.

4. The endoscope sleeve of claim 3, wherein the sealing mechanism comprises at least one of an elastomeric material, self-fusing silicon tape, hook and loop fastener, purse string closure, tie-on closure, or pressure sensitive adhesive tape.

5. The endoscope sleeve of claim 1, further comprising a fluid port in fluid connection with the cavity.

6. The endoscope sleeve of claim 5, wherein the fluid port is connected to at least one of the first sleeve and the second sleeve.

7. The endoscope sleeve of claim 1, wherein the distal end of the sleeve comprises a closure for closing the lumen.

8. The endoscope sleeve of claim 7, wherein the closure is a re-sealable zipper.

9. The endoscope sleeve of claim 1, further comprising a wiping material disposed on an inner surface of the sleeve.

10. The endoscope sleeve of claim 9, wherein the wiping material comprises at least one of a hydrophilic foam, gauze, or an unwoven material.

11. The endoscope sleeve of claim 1, further comprising a wiping material disposed within the cavity.

12. The endoscope sleeve of claim 1, wherein the sleeve comprises a first sleeve and the retainer comprises a second sleeve including a perforation, wherein the first sleeve is detachable at the perforation.

13. The endoscope sleeve of claim 1, wherein at least a portion of the sleeve comprises at least one of a transparent material and an elastomeric material.

14. The endoscope sleeve of claim 1, wherein at least a portion of the sleeve comprises a flexible material.

15. The endoscope sleeve of claim 1, wherein the sleeve in the extended configuration has a length longer than the length of the sleeve in the compact configuration.

16. The endoscope sleeve of claim 1, wherein the sleeve has the compact configuration when the retainer is attached to the sleeve.

17. The endoscope sleeve of claim 1, wherein the second sleeve is removably attached at or between a midsection and the distal end of the first sleeve.

18. The endoscope sleeve of claim 1, wherein the sleeve comprises a line of weakness extending from the proximal end to the distal end,
wherein the line of weakness allows the sleeve to be separated along the line of weakness.

19. The endoscope sleeve of claim 1, wherein at least a portion of the sleeve comprises a material that has reduced friction when sliding over the endoscope.

20. The endoscope sleeve of claim 1, further comprising an annular squeegee disposed within the lumen, wherein the annular squeegee has an inner circumference and an outer circumference, wherein the annular squeegee is attached to an inner surface of the sleeve along the outer circumference of the annular squeegee.

21. An endoscope sleeve comprising:
a sleeve defining a lumen for accepting an endoscope in a slidable manner, the sleeve having a proximal end configured to accept the endoscope and a distal end configured to be slidably disposed over the endoscope, wherein the sleeve comprises a compact configuration and an extended configuration; and
a retainer configured to be detachably attached to the sleeve, wherein in the compact configuration the retainer is attached to the sleeve and in the extended configuration the retainer is detached from the sleeve allowing the sleeve to be extendable over the endoscope,
wherein the sleeve comprises a first sleeve and the retainer comprises a second sleeve, and the second sleeve defines the lumen for accepting the endoscope,
wherein the second sleeve has a length that is less than a length of the first sleeve, and
wherein the second sleeve includes a proximal end and a distal end, and the proximal ends of the first and second sleeves are attached and the distal end of the second sleeve is removably attached to the first sleeve away from the proximal end of the first sleeve.

22. The endoscope sleeve of claim 21, wherein the second sleeve is removably attached at or between a midsection and the distal end of the first sleeve.

* * * * *